United States Patent [19]

Lasker

[11] Patent Number: 4,533,549
[45] Date of Patent: Aug. 6, 1985

[54] ANTITHROMBOTIC AGENT

[76] Inventor: Sigmund E. Lasker, Rivercross, Roosevelt Island, New York, N.Y. 10044

[21] Appl. No.: 580,761

[22] Filed: Feb. 17, 1984

Related U.S. Application Data

[63] Continuation of Ser. No. 455,517, Jan. 4, 1983, abandoned, which is a continuation of Ser. No. 223,010, Jan. 6, 1981, abandoned.

[51] Int. Cl.$^3$ ..................... A61K 31/725; C08B 37/10
[52] U.S. Cl. ....................................... 514/56; 536/21; 514/822
[58] Field of Search ................... 536/21; 424/180, 183

[56]  References Cited
U.S. PATENT DOCUMENTS

| | | | |
|---|---|---|---|
| 3,766,167 | 10/1973 | Lasker | 536/21 |
| 4,119,774 | 10/1978 | Andersson et al. | 536/21 |
| 4,122,250 | 10/1978 | Schmer | 536/21 |
| 4,175,182 | 11/1979 | Schmer | 536/21 |
| 4,281,108 | 7/1981 | Fussi | 424/183 |

OTHER PUBLICATIONS

Lasker, Adv. Exp. Med. Biol., vol. 52, pp. 119–130, 1975.
Lasker, Federation Proceedings, vol. 36, pp. 92–97, 1977.
Andersson et al., Thrombosis Research, vol. 9, pp. 575–583, 1976.
Hook et al., FEBS Letters, vol. 66, pp. 90–93, 1976.

*Primary Examiner*—Blondel Hazel
*Attorney, Agent, or Firm*—St. Onge Steward Johnston & Reens

[57] ABSTRACT

The object of the invention is to provide a new antithrombotic agent.

Coagulation of blood acts through a cascade of stages, the mechanisms and interaction of which have not been fully clarified. The present invention provides a derivative of heparin which can be administered orally, topically, or parenterally to antagonize the effect of factor Xa to a greater extent than commercial porcine heparin. In addition, the derivative has insignificant USP anticoagulant and platelet aggregating activities.

The heparin derivative according to the invention, has a molecular weight of from about 2,500 to about 4,000 daltons, gives a positive metachromatic test for sulfated polysaccharides. Preferably, when isolated as the sodium salt, the derivative contains by elemental analysis about 26.2% carbon, 4.33% hydrogen, 1.98% nitrogen, 7.1% sulfur, and 9.8% sodium, the molar ratio C:N:S:Na being about 10:1.5:2:4.

9 Claims, No Drawings

ANTITHROMBOTIC AGENT

This is a continuation of application Ser. No. 455,517, filed Jan. 4, 1983, which in turn was a continuation of U.S. Ser. No. 223,010, filed Jan. 6, 1981, both of these prior applications now being abandoned.

DESCRIPTION

Technical Field

My invention relates to a new heparin-derived antithrombotic agent having maximal anti-activated coagulation factor Xa activity, yet insignificant USP anticoagulant and platelet aggregating activities.

A substance with potent blood anticoagulant properties was first isolated by McLean in 1916 from bovine liver and heart; it was called heparin. Subsequently, similar substances have been isolated from a variety of mammalian tissues including whale lung and liver, and animal and human tumors. Potent anti-coagulants with comparable structure have also been isolated from such disparate sources as fish scales and other organs of fish and from the common surf and ocean clam. All are heterogeneous polyelectrolytes containing sulfate, uronic acid, and glucosamine. Although detailed structural data are generally unavailable, these preparations are often also called heparin. Most of the investigative work has been based on the clinically available commercial porcine mucosal and bovine lung preparations and, thus, the term "heparin" generally refers to commercial preparations.

It is now apparent that heparin is a family appellation for polysaccharides varying considerably in physical and biological properties, that contain 2-acetamido-2-deoxy-alpha-D-glucopyranosyl and alpha-D-glucopyranosyl uronic and alpha-L-idopyranosyl uronic acid residues with varying proportions of N-acetyl, O-sulfate and N-sulfate. In addition, any given preparation is a molecular admixture of components that can be fractionated by a variety of procedures into a series of apparent homologs.

Blood clots of all kinds contribute to the fatality of many diseases. Pulmonary emboli are estimated to occur in three-quarters of a million patients a year. Most of these pulmonary emboli originate from deep vein thrombosis induced by a variety of stimuli including venous stasis in hospitalized and sedentary middle aged patients. Treatment with heparin has become accepted clinical practice to prevent the formation of the emboli.

In addition, tissue damage induced by surgery, malignancy, burns, infection or normal delivery can release tissue thromboplastin. Thromboplastin is a complex mixture of compositions having several different types of activity. Infections, vessel damage or the presence of foreign surfaces from prosthesis devices also serve as stimuli for the release of several coagulation factors, namely, the activated forms of coagulation factors XII, XI, and IX. Estrogens increase the levels of coagulation factors VII, IX, X, XI and XII.

In the presence of certain stimuli, the body produces antithrombin III, a naturally-occurring thrombin inhibitor. Estrogens, for example, are known to slow the antithrombin III reaction. Low levels of antithrombin III in the blood have been associated with recurrent thrombosis while excessive amounts have been related to bleeding tendencies.

Despite the long clinical use of heparin as an anticoagulant, much is still unknown as to how it intercedes in the coagulation process. It appears that a major function of heparin is to accelerate the capacity of antithrombin III to neutralize the proteolytic activity of the activated forms of coagulation factors Xa, XI, IX, thrombin and plasmin. There are profound differences in the rates of inhibition of these various coagulation factors by heparin. Moreover, the protection against thrombosis can bring about adverse bleeding tendencies.

The physiologic importance of heparin in the various steps of the cascade of coagulation reactions has not been clearly established. However, the effect of heparin on activated coagulation factor Xa could be more important than the neutralization of thrombin, a step that occurs before intravasular coagulation begins.

Background Art

In an earlier patent, U.S. Pat. No. 3,766,167, I disclosed an orally-effective anticoagulant derived from heparin by controlled hydrolysis. The disclosed anticoagulant, isolated as a sodium salt of polysaccharide, was soluble in water, insoluble in acetone and ethanol, contained glucosamine, glucuronic acid and iduronic acid, had a molecular weight of 5300 daltons, contained by elemental analysis about 22% carbon, 3.6% hydrogen, 2.5% nitrogen, 11.4% sulfur, and 13.2% sodium, the molar ratio C:N:S:Na being about 10:1:2:3; and gave a positive metachromatic test. The anticoagulant could be in the form of the free acid and pharmacologically acceptable salts of said acid. This derivative of heparin is advantageous in that it can be administered orally; however, like the base heparin, it retained USP anticoagulation activity, platelet aggregating activity and offered little increase in anti-activated coagulation factor X activity.

In a publication appearing in FEDERATION PROCEEDINGS, Vol. 36, No. 1, January, 1977, at pages 92–97, I discussed my investigations on the heterogeneity of heparins. One sample tested was depolymerized commercial heparin exhibiting a molecular weight of about 5,300 daltons. This sample was fractionated into several narrower molecular weight fractions, the lowest of which was about 3,260 daltons. This latter fraction showed the lowest USP anticoagulant activity of those tested. However, even the lowest molecular weight fraction is shown in Table 2 to retain significant USP anticoagulant activity, in this case being 45 units. Also discussed was the variation of platelet aggregating effect of six heparin fractions with changes in ionic strength. I reported there that higher molecular weight fractions tended to be more active and more sensitive to salt concentration than low molecular weight fractions. This combination of properties makes the compounds disclosed therein significantly different in physiologic effect from those of my present invention.

In a publication by L. O. Anderson et al, appearing in THROMBOSIS RESEARCH, Vol. 9, 1966, pages 575–583, the anticoagulant properties of heparin fractionated by affinity chromatography and gel filtration are discussed. Fractions having molecular weights of from 5,000 to 40,000 daltons were tested for anticoagulant activities by the APTT multiple role method and an anti factor Xa specific method. The results showed wide divergence in values for both lower and higher molecular weight fractions. For the low molecular weight material, it was reported that the specific activity may be up to twelve times greater than the multiple role activity. For high molecular weight fractions, the activities appeared to reverse. The authors caution, however, that too much emphasis should not be laid on molecular weight as a parameter of importance in itself in relation to activity.

In an artile by M. Hook et al in FEBS LETTERS, Vol. 66, No. 1, July 1976, pages 90–93, the authors present their findings regarding the separation of high and low activity species of heparin by affinity chromatography on immobilized antithrombin. They indicate that the low and high activity fractions showed essentially similar molecular-size distributions.

Despite the great amount of research done to date to elucidate the physiologic importance of heparin and its derivatives in the various stages of the coagulation cascade, there remains a present need for a composition which provides a high degree of safety with therapeutic effectiveness. Until the present invention, there has not been a composition which provided a maximal anti-activated coagulation factor Xa activity, yet exhibited insignificant USP anticoagulant and platelet aggregating activities.

Disclosure of Invention

I have now discovered a composition which has this desirable combination of properties. The composition has insignificant anticoagulant activity when measured by the classical USP assay method. By this I mean less than 40 USP XVIII units, and preferably less than about 20 USP XVIII units. In one preferred embodiment it has an anticoagulant activity in the order of only 13 USP XVIII units, compared to 160 USP XVIII units for commercial porcine heparin. On the other hand, the new composition has at least as great, and preferably an appreciably greater, anti-activated coagulation factor Xa activity than commercial porcine heparin, namely, about 150 units/mg. One preferred embodiment has an anti-activated coagulation factor Xa activity of about 190 units/mg. The composition of this invention thus retains and preferably exceeds an important virtue of heparin, i.e., it interacts directly with a component of the coagulation cascade and in addition interacts minimally with the coagulation cascade at the level of thrombin production. Additionally, it has minimal platelet aggregating activity. It is believed that this combination of properties will make it safer under many circumstances than commercial porcine heparin.

I have discovered that by depolymerizing and fractionating either heparin residues, commercial porcine heparin (i.e., heparin isolated from porcine intestinal mucosa), bovine heparin, or marine heparinoids, having a molecular weight of about 12,500 daltons, it is possible to obtain an orally-active anti-thrombotic agent having a molecular weight of from about 2,500 to about 4,000 daltons as determined by standard equilibrium ultracentrifugation techniques. All molecular weights referred to herein are weight average molecular weights. Preferably, the composition of the invention will exhibit an average molecular weight of about 3,500 daltons.

The antithrombotic agent of this invention is a mucopolysaccharide. It gives a positive metachromatic test for sulfated polysaccharides. It is completely soluble in water and insoluble in both acetone and ethanol. By elemental analysis, the sodium salt as isolated preferably contains about 26.2% carbon, 4.33% hydrogen, 1.98% nitrogen, 7.1% sulfur and 9.8% sodium. The molar ratio C:N:S:Na is preferably about 10:1.5:2:4.

The composition contains induronic acid, glucuronic acid and glucosamine (hexosamine) which may be cleaved by acid hydrolysis and separated.

The iduronic acid content of the antithrombotic agent of this invention as determined by the Conrad method is preferably about 43%, compared to 56% for commercial porcine heparin. The composition may be further distinguished from commercial porcine heparin by a preferred hexosamine content of about 20.3%, a preferred nitrogen content of about 1.98%, a preferred sulfur content of about 7.1%, and a molecular weight of from about 2,500 to about 4,000 daltons for the composition versus a hexosamine content of 23.1%, a nitrogen content of 1.95%, a sulfur content of 12.0% and a molecular weight of about 12,500 daltons for commercial porcine heparin. The composition can also be differentiated from commercial porcine heparin by its NMR spectrum.

The antithrombotic agent of the invention may be prepared by depolymerizing either heparin residues, commercial porcine or bovine heparin, or marine heparinoids. Suitable isolation techniques may also be employed. Depolymerization can be done by a variety of methods, including the use of nitrous acid at 0° C., the enzyme heparinase, and reaction with a blend of ascorbic acid and hydrogen peroxide. The reaction products can then be isolated and fractionated by a suitable technique such as precipitation using an organic solvent, such as ethanol, methanol, acetone, methyl ethyl ketone or dioxane. When the nitrous acid procedure is employed, for example, the time and temperature should be controlled to yield a product with the desired properties. Because each lot of heparin may respond differently, the person of ordinary skill in the art will be aware that several test runs may be necessary to achieve the desired combination of properties. One quick check would be for the degree of loss of metachromatic color, where a complete loss would indicate complete depolymerization—meaning the reaction had gone too far.

The composition is preferably isolated in the form of a sodium salt. It may readily be converted to the free acid, to another metallic salt or to an acid addition salt. Since the free acid form is unstable, it would not appear to be of clinical interest. The composition contains a carboxyl group; accordingly, acid addition salts can be prepared from acids which give a higher hydrogen ion concentration than does the carboxyl group. It presently appears that the sodium salt will be the antithrombotic agent of choice, but for many therapeutic uses the compound isolated will often be converted to pharmacologically acceptable salts which as aforesaid may be either metallic salts or acid addition salts. Metallic salts may be prepared from alkali metal and alkaline earth metal bases, preferably hydroxides. Acid addition salts may be prepared from acids, such as hydrochloric, sulfuric, phosphoric, citric, and the like.

For the preparation of the acid salts it is convenient to simply titrate a water solution of the compound as isolated with a solution of the selected acid. Metallic salts may be prepared, for example, by passing a solution of the isolated sodium salt over a sulfonated polystyrene ion exchange resin on the acid cycle and treating the eluate with a dilute solution of the selected salt, suitably in the form of the hydroxide. In both instances, the desired product can be obtained by freeze-drying.

The products of this invention are particularly useful as antithrombotic agents in mammals. The physician or veterinarian will determine a dosage which will be most suitable for a particular application. It may vary from patient to patient depending upon the size of the patient, the condition under treatment, mode of administration, and other circumstances, particularly levels of prothrombin and other coagulation factors. All of these circumstances are readily evaluated by those skilled in the art.

Although it is presently believed that the compounds of this invention will be most useful for oral administration, they may be administered topically or parenterally, for example, by intravenous or intramuscular injection. The products will normally be made available at a variety of dosage levels since, as is well known, different subjects, and even the same subject, will require different dosage levels for any of a number of reasons at the time of the administration of the therapeutic agent. For example, dosage units containing from about 100 to about 500 mg. may be useful.

The products of this invention may be administered alone but will generally be administered with a pharmaceutically-acceptable, nontoxic-carrier or synergist, the proportions of which are determined by the suitability and chemical nature of the particular carrier or synergist, the chosen rate of administration and standard pharmaceutical practice. For maintaining therapeutically effective levels in the blood, they will normally be administered orally in the form of tablets or capsules containing such water-soluble excipients as starch, sugar, certain types of clay, and the like. Dosage units may be prepared in the form of sterile water solutions containing other solutes, for example, enough saline or glucose to make the solution isotonic.

BEST MODE FOR CARRYING OUT THE INVENTION

The following example is given by way of illustration only and is not to be considered limiting of this invention. Unless otherwise indicated, all parts and percentages are by weight.

EXAMPLE 1

Depolymerization with Ascorbic Acid-Hydrogen Peroxide Mixture 27 grams of ascorbic acid and 78.12 ml. of 30% hydrogen peroxide are incubated with 35 grams of a commercial porcine heparin preparation in 7.8 liters of a buffered solution at pH 7.8 consisting of 0.2M phosphate buffer in 1M NaCl. The reaction mixture is agitated for 24 hours at 22° C. and protected from ambient light.

Isolation and Fractionation of Reaction Products

After the reactants are exhausted—usually 24 hours—the volume of the reaction mixture is reduced by flash evaporation and the resulting solution freed of salts and buffer by dialysis until the dialysate is free of crystalloids. The product remaining in the dialysis sack is lyophylized and the yield of product calculated.

Fractionation is achieved by adding an organic solvent, namely absolute ethanol, dropwise to a 3% solution of the depolymerized product at room temperature with stirring. Addition of ethanol is stopped when the mixture appears turbid. Centrifugation at moderate speed is used to remove the precipitate. This process of addition of ethanol and centrifugation is repeated until no further turbidity results when ethanol is added. Sodium chloride is added to the final nonturbid mixture to make a 1 molar solution. The precipitate that is obtained on the addition of sodium chloride is removed by centrifugation. The salted out fraction is freed of sodium chloride by column chromatography with Sephadex G-25. The fraction prepared in this manner is analyzed, and compared to commercial porcine heparin as indicated:

|  | Composition of the invention | Commercial porcine Heparin |
|---|---|---|
| Anticoagulant Activity USP XVIII (1) | 13 | 160 |
| Anti-activated Coagulation Factor Xa (2) Activity (units/mg) | 190 | 150 |
| Platelet Aggregating Activity (3) | 0 | +++ |
| Induronic Acid (%) | 43 | 56 |
| Hexosamine (%) | 20.3 | 23.1 |
| Carbon (%) | 26.2 | 23.1 |
| Hydrogen (%) | 4.33 | 5.1 |
| Nitrogen (%) | 1.98 | 1.95 |
| Sulfur (%) | 7.1 | 12.0 |
| Sodium (%) | 9.8 | 13.2 |
| Molecular Weight (daltons) | 3,500 | 12,500 |

(1) Test method as reported in the United States Pharmacopeia XVIII, Page 629.
(2) Test method as reported by Yin, Et., S. Wessler and J. V. Butler in J. Lab. Clin. Med. 81,298,1973.
(3) Determined by a platelet aggregation test which is a modification of the standard aggregometer measurement and is based on a direct measurement of microscopic platelet aggregates above a critical predetermined size. The scale extends from 0, indicating no aggregation, to +++, indicating maximum aggregation.

The above description is for the purpose of teaching the person skilled in the art how to practice the present invention. This description is not intended to detail all of the obvious modifications and variations of the invention which will become apparent upon reading. However, applicant does intend to include all such obvious modifications and variations within the scope of his invention which is defined by the following claims.

What is claimed is:

1. An antithrombotic agent derived from heparin having an anticoagulant activity of less than 20 USP XVIII units and insignificant platelet aggregating activity, and an anti-activated coagulation factor Xa activity of from about 150 to about 190 units/mg, said agent being a pharmacologically acceptable salt of a mucopolysaccharide soluble in water, insoluble in acetone and ethanol, containing glucosamine, glucuronic acid and iduronic acid, having a weight average molecular weight of from about 2,500 to about 4,000 daltons, giving a positive metachromatic test for sulfated polysaccharides.

2. An antithrombotic agent according to claim 1 having an anticoagulant activity of about 13 USP XVIII units.

3. An antithrombotic agent according to claim 1 which is derived from a member selected from the group consisting of porcine heparin, bovine heparin, heparin residues and marine heparinoids.

4. An antithrombotic agent according to claim 3 which is derived from porcine heparin.

5. An antithrombotic agent according to claim 1 wherein the weight average molecular weight is about 3,500 daltons.

6. An antithrombotic agent according to claim 1 which, when isolated as a sodium salt, contains by elemental analysis about 26.2% carbon, 4.33% hydrogen, 1.98% nitrogen, 7.1% sulfur, and 9.8% sodium, the molar ratio C:N:S:Na being about 10:1.5:2:4.

7. A dosage form of the antithrombotic agent of claim 1 comprising from about 100 to about 500 mg. of said agent in a pharmaceutically acceptable carrier.

8. A dosage form according to claim 7 wherein the carrier comprises a solid, water-soluble excipient.

9. A dosage form according to claim 7 wherein the carrier comprises sterile water.

* * * * *